US008741320B2

(12) United States Patent
Raschke et al.

(10) Patent No.: US 8,741,320 B2
(45) Date of Patent: Jun. 3, 2014

(54) SPHERICAL COSMETIC PREPARATIONS FOR TOPICAL APPLICATION

(75) Inventors: Thomas Raschke, Pinneberg (DE); Frank Hetzel, Welle (DE); Volker Kallmayer, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1856 days.

(21) Appl. No.: 10/569,381

(22) PCT Filed: Aug. 26, 2004

(86) PCT No.: PCT/EP2004/009518
§ 371 (c)(1), (2), (4) Date: Sep. 1, 2006

(87) PCT Pub. No.: WO2005/020949
PCT Pub. Date: Mar. 10, 2005

(65) Prior Publication Data
US 2007/0196400 A1 Aug. 23, 2007

(30) Foreign Application Priority Data

Aug. 27, 2003 (DE) .................. 103 39 747
Aug. 30, 2003 (DE) .................. 103 40 106
Dec. 10, 2003 (DE) .................. 103 57 640

(51) Int. Cl.
A61K 8/02 (2006.01)
A61K 8/30 (2006.01)

(52) U.S. Cl.
USPC ........................ 424/401; 424/70.31

(58) Field of Classification Search
None
See application file for complete search history.

(56) References Cited

U.S. PATENT DOCUMENTS

| 4,675,236 | A | 6/1987 | Ohkawara et al. |
| 4,880,634 | A | 11/1989 | Speiser |
| 5,686,112 | A | 11/1997 | Liedtke et al. |
| 5,705,217 | A | 1/1998 | Aasted |
| 5,785,976 | A | 7/1998 | Westesen et al. |
| 5,807,572 | A * | 9/1998 | Kim et al. ............... 424/450 |
| 5,885,486 | A | 3/1999 | Westesen et al. |
| 6,156,804 | A | 12/2000 | Chevalier et al. |
| 6,207,178 | B1 | 3/2001 | Westesen et al. |
| 6,531,160 | B2 | 3/2003 | Biatry et al. |
| 6,534,091 | B1 | 3/2003 | Garces et al. |
| 6,818,296 | B1 | 11/2004 | Garces et al. |
| 6,823,649 | B1 | 11/2004 | Pauchet |
| 2002/0022038 | A1 | 2/2002 | Biatry et al. |
| 2002/0102282 | A1 | 8/2002 | Bleckmann et al. |
| 2003/0044469 | A1 | 3/2003 | Viladot Petit et al. |
| 2003/0064106 | A1 | 4/2003 | Garces et al. |
| 2004/0005283 | A1 | 1/2004 | Cernasov et al. |
| 2004/0223989 | A1 | 11/2004 | Auguste et al. |
| 2004/0258721 | A1 | 12/2004 | Bauer et al. |

FOREIGN PATENT DOCUMENTS

| CH | 692968 | 1/2003 |
| DE | 4223004 | 1/1994 |
| DE | 9321186 | 9/1996 |
| DE | 19852262 | 5/2000 |
| DE | 19945203 | 12/2000 |
| DE | 10044062 | 4/2002 |
| DE | 10059668 | 6/2002 |
| DE | 10148313 | 4/2003 |
| DE | 10209111 | 9/2003 |
| DE | 10210449 | 9/2003 |
| EP | 0167825 | 1/1986 |
| EP | 0234078 | 9/1987 |
| EP | 0529396 | 3/1993 |
| EP | 0934743 | 8/1999 |
| EP | 0998910 | 5/2000 |
| EP | 1064911 | 1/2001 |
| EP | 1064912 | 1/2001 |
| EP | 1129771 | 9/2001 |
| EP | 1192935 | 4/2002 |
| EP | 1201219 | 5/2002 |
| EP | 1473016 | 11/2004 |
| JP | 10-182337 | 7/1998 |
| JP | 2001-348310 | 12/2001 |
| JP | 2003-73230 | 3/2003 |
| WO | 94/20072 | 9/1994 |
| WO | 00/10522 | 3/2000 |
| WO | 00/67728 | 11/2000 |
| WO | 01/03538 | 1/2001 |
| WO | 01/38174 | 5/2001 |
| WO | 03/075881 | 9/2003 |
| WO | 2005/020940 | 3/2005 |

OTHER PUBLICATIONS

Le Joliff et al, Translation of WO01/03538, European Patent Office, pp. 1-4.*
The Free Dictionary, http://www.thefreedictionary.com/dispersed, last accessed Nov. 19, 2013.*
The Free Dictionary, http://www.thefreedictionary.com/emulsion, last accessed Nov. 19, 2013.*
English Language Abstract of DE 198 46 772.
English language abstract of EP 0529396.
English language abstract of JP 10-182337.
English language abstract of JP 2003-73230.
English language abstract of JP 2001-348310.
English Language Abstract of DE 102 09 111.
English Language Abstract of EP 1 201 219.
English Language Abstract of DE 100 59 668.
English Language Abstract of DE 199 45 203.
English Language Abstract of DE 198 52 262.
English Language Abstract of CH 692 968.

* cited by examiner

*Primary Examiner* — Trevor Love
(74) *Attorney, Agent, or Firm* — Abel Law Group, LLP

(57) ABSTRACT

A cosmetic or dermatological preparation based on a W/O emulsion which is present as a plurality of shaped bodies. The shaped bodies are solid, semisolid and/or dimensionally stable at room temperature and comprise one or more of a wax, a lipid, an emulsifier, a natural polymer and a synthetic polymer.

20 Claims, No Drawings

SPHERICAL COSMETIC PREPARATIONS FOR TOPICAL APPLICATION

CROSS-REFERENCE TO RELATED APPLICATIONS

The present application is a U.S. National Stage of International Application No. PCT/EP2004/009518, filed Aug. 26, 2004, which claims priority of German Patent Application No. 103 39 747.7, filed Aug. 27, 2003, German Patent Application No. 103 40 106.7, filed Aug. 30, 2003, and German Patent Application No. 103 57 640.1, filed Dec. 10, 2003.

BACKGROUND OF THE INVENTION

1. Field of the Invention

The invention relates to a cosmetic and/or dermatological preparation for topical application based on a water-containing emulsion in the form of solid, semisolid and/or dimensionally stable spheres, spheroids or otherwise shaped bodies containing essentially waxes, emulsifiers, natural and/or synthetic polymers and/or mixtures thereof. The preparation melts upon rubbing and/or distribution on the skin and/or the hair and/or becomes completely or partially liquid due to shear forces and/or mixes with the lipids of the skin sebum and/or dissolves therein.

2. Discussion of Background Information

Tablets for peroral pharmaceutical use have been known since the 19th century at the latest. These are single-dose solid medicaments which are formed from dry powders, crystals or granules under high pressure and in the presence of auxiliaries (Rudolf Voigt, "Pharmazeutische Technologie" [Pharmaceutical Technology], Deutsche Apotheker Verlag, Stuttgart, 9th edition (2000), p. 163 ff).

Suppositories for rectal or vaginal use have also been used in pharmacy for a long time. These are dimensionally stable preparations which melt at body temperature or slowly dissolve in aqueous medium (Rudolf Voigt, "Pharmazeutische Technologie" [Pharmaceutical Technology], Deutsche Apotheker Verlag, Stuttgart, 9th edition (2000), p. 267 ff). They can be produced by molding or compression. Depending on the manufacturing process, besides the customary pharmaceutical requirements, such as good tolerability and compatibility with the active ingredient and durability, further requirements are placed on the raw materials used, such as, for example, small differences between the melting point and solidification point, and between the yield point and clear melting point and at least kinetic stability of the crystal modification formed first. Suppositories for topical use have not hitherto been described.

Moreover, the prior art discloses pharmaceutical capsules, for example soft and hard gelatin capsules, which consist of an envelope of gelatin and glycerol, and sometimes dyes, and a liquid, pasty or particulate filling. The method of producing these capsules known for many years takes place, for example, in accordance with the so-called rotary-die system (Seifen-Öle-Fette-Wachse, Vol. 113; No. 3/1987, page 67 ff). These gelatin capsules dissolve when swallowed in the gastrointestinal tract and release their ingredients. Since it is directly possible to produce capsules in different sizes and shapes, use is limited not just to peroral application forms (Rudolf Voigt, "Pharmazeutische Technologie" [Pharmaceutical Technology], Deutsche Apotheker Verlag, Stuttgart, 9th edition (2000), p. 543ff). Oral absorption can be achieved through suckable capsules. They are hollow on the inside and have a wall which is three times thicker than that of other capsules. The active ingredient is incorporated here in the gelatin envelope. A further example is nitroglycerol chewable capsules (bite-through capsules), which likewise allow rapid absorption of the active ingredient via the oral mucosa. Furthermore, individually dosed medicaments can be applied after puncturing or cutting the tubular ointment capsules by squeezing out the contents (percutaneous application of nitroglycerol heart ointment).

From the food sector, for example, various preparations which are solid at room temperature are known which melt at body temperature. These are mostly vegetable fat preparations, particularly based on cocoa butter and shea butter (chocolate) or W/O emulsions of hydrogenated vegetable fats and free fatty acids (margarine). As "ice confection", preparations are known in which a moderately high enthalpy of melt has to be applied and which therefore have a cooling effect in the mouth.

Moreover, pralines are known which comprise liquid or pasty ingredients in a dimensionally stable chocolate coating. The coating melts during sucking or biting-through in the mouth or after swallowing.

In the cosmetics sector, the so-called bath beads are known whose envelope, e.g. made of gelatin, dissolves in hot or warm bathwater without leaving a residue and releases its contents, for example surfactant preparations, emulsions, lipids, dyes and/or perfumes, into the bathwater. Since the envelope consists of gelatin, the product must not contain water, otherwise the envelope would soften during storage.

A second group of cosmetic capsules covers all products for which the capsule envelope represents only a container for the single dose and use and whose envelope is left behind following use. A disadvantage with this is that the envelope which is left behind is troublesome and in addition has to be disposed of.

Numerous cosmetic and/or dermatological active ingredients are unstable toward certain influences such as moisture, low or high pH values and oxygen or light. There has therefore been no lack of attempts to remove the specified undesired environmental influences from such active ingredients in such a way that the active ingredients are nevertheless released upon application. One way of achieving this aim is the microencapsulation or nanoencapsulation of active ingredients. The encapsulation material as carrier system for the active ingredients allows them to be incorporated into suitable preparations in a form protected against environmental influences without the user being able to perceive the capsules during product application.

The aim of such an encapsulation is, for example, to produce wax particles containing active ingredient in the micrometer range (1-250 µm) which can be incorporated into common pasty or liquid cosmetic preparations. It is hitherto not known to produce, store and topically use these microcapsules as an independent cosmetic preparation.

There are a number of approaches for encapsulating cosmetic active ingredients. For example, the liposomal encapsulation of medicaments, which is intended to lead to a slow release of active ingredient, is known. These are essentially spherical vesicles containing active ingredient and surrounded by phospholipids or other amphiphilic agents, the so-called liposomes. The long-term stability of such structures, however, is poor.

Nanoparticles are solid particles with particle sizes of from 20 to 500 nm. Sometimes, larger particles with diameters up to 1000 nm are also regarded as being nanoparticles. Particles of this type generally consist of polymers and have cavities or form an envelope so that guest molecules can stay inside them, these molecules being enclosed or adsorbed. These guest molecules are then slowly released upon application of the nanoparticle-containing product. Solid lipid nanoparticles, which comprise active ingredients distributed within a matrix made of solid lipids behave in a similar way. The size of the particles is comparable with that of nanoparticles.

Numerous methods are known for encapsulating pharmaceutical or cosmetic active ingredients for controlling active ingredient release or the stable incorporation in preparations.

European patent application EP 1064911 or EP 1064912 discloses microcapsules comprising active ingredients and having a diameter of from 0.1 to 5 mm which are obtained by preparing a matrix from gel formers, chitosan and active ingredient, and adding this dropwise to aqueous solutions of anionic polymers. In so doing, a membrane forms from chitosan and anionic polymer and surrounds the active ingredient solution. These microparticles are then in turn used as a constituent of customary cosmetic preparations. General information regarding encapsulation techniques with chitosan can be found in Journal of Microencapsulation 14, pages 689-711 (1997).

Mostly lipophilic active ingredients encapsulated in lipid particles are known per se to the person skilled in the art. For example, EP 167825, DE 100 59 668, DE 199 45 203, EP 0934743, WO 94/20072, WO 00/10522 and WO 00/67728 describe lipid particles charged with active ingredient. However, these documents were unable to solve the problem of providing spherical preparations with or without cosmetic ingredients which can be prepared, stored and applied topically as an independent cosmetic preparation.

Lip care sticks made of W/O emulsions which are solid at room temperature are described, for example, in DE 10148313. This technology described therein is hereby subject-matter of the present invention. The emulsions according to DE 10148313 do not become liquid upon distribution or rubbing on the skin, the emulsion is merely rubbed off onto the area of application, particularly the lips. Liquefaction of the preparations described therein is even undesired since, to care for the lips, the applied material should remain for as long as possible at the site of application and not, for example, run off.

It is an object of the present invention to provide a cosmetic preparation which is in the form of dimensionally stable spheres, is thus individually portionable and can be distributed as a whole on the skin. In this connection, no residues, capsule material etc. at all should be left behind which would, if appropriate, have to be disposed of separately or remain visible on the skin. In particular, it is the object of the present invention to provide a cosmetic preparation which constitutes a novel cosmetic product form and offers the user a novel application experience and broadens the application spectrum of skincare and/or hair care products.

SUMMARY OF THE INVENTION

The present invention provides a cosmetic and/or dermatological preparation based on a W/O emulsion which is present as a plurality of shaped bodies which are solid, semisolid and/or dimensionally stable and comprise one or more of a wax, a lipid, an emulsifier, a natural polymer and a synthetic polymer.

In one aspect of the preparation, the shaped bodies may comprise a sphere and/or a spheroid.

In another aspect, the shaped bodies may be solid, semisolid and/or dimensionally stable up to a temperature of at least 35° C.

In yet another aspect, the preparation may comprise one or more waxes selected from microcrystalline waxes, paraffin waxes, ester waxes, glyceride waxes, fatty alcohols, solid emulsifiers and combinations thereof. For example, the one or more waxes may comprise one or more of cetyl palmitate, cetyl ricinoleate, beeswax, hydrogenated cocoglycerides, methyl palmitate, candelilla wax, carnauba wax, paraffin wax, ceresine, ozokerite, myristyl myristate, tripalmitin, tribehenin, glyceryl palmitostearate, hydrogenated rapeseed oil, and C15-C40 alkylstearyl stearate.

In another aspect, the preparation may comprise a dimensionally stable lipid/emulsifier mixture which comprises dispersed water having a droplet size below 50 micrometers.

In another aspect of the preparation, the shaped bodies may have an average diameter of from 3 mm to 40 mm and/or the shaped bodies may comprise predominantly spherical, round or ellipsoidal shapes and/or the shaped bodies may have a volume of from 0.1 ml to 20 ml.

In yet another aspect, the preparation may further comprise one or more substances selected from auxiliaries, UV filters, pigments, active ingredients, dyes, sensory additives, thickeners, gel formers, preservatives, antioxidants, complexing agents, flavorings, denaturants, and perfumes.

In a still further aspect of the preparation, the shaped bodies may be individually enclosed by a packaging envelope.

In another aspect, the shaped bodies may be packaged individually or in a number of two or more in a pack, e.g., a blister pack, made of at least one of paper, metal and plastic.

In another aspect, the preparation may be packaged in ready-made portions in a blister pack for individual removal, or the shaped bodies may be packaged in a dispenser system.

In another aspect of the preparation of the present invention, the shaped bodies may melt upon rubbing and/or distributing them on the skin or the hair; and/or become completely or partially liquid due to shear forces; and/or dissolve completely or partially in skin sebum lipids.

In a still further aspect, the preparation may comprise at least two shaped bodies which differ from each other in one or more of their appearance, their ingredients and their purpose.

The present invention also provides a method of applying a cosmetic ingredient and/or a dermatological ingredient to skin or hair. The method comprises rubbing and/or distributing on the skin or hair a preparation according to the present invention, including the various aspects thereof set forth above, which comprises the cosmetic ingredient and/or dermatological ingredient.

The present invention also provides a method of applying cosmetics without leaving a residue on skin. The method comprises applying the preparation of the present invention, including the various aspects thereof set forth above, to the skin.

DETAILED DESCRIPTION OF THE INVENTION

It was surprising and extraordinarily astonishing for the person skilled in the art that the set of objects can be achieved by a cosmetic and/or dermatological preparation in the form of solid, semisolid and/or dimensionally stable spheres, spheroids or otherwise shaped bodies comprising a W/O emulsion comprising essentially waxes, lipids, emulsifiers, natural and/or synthetic polymers and/or mixtures thereof. Under storage conditions, i.e. room temperature or lower, the preparations are completely or partially solid.

The advantage and at the same time the property according to the invention of the capsule-like preparation is that it melts upon rubbing and/or distributing the capsule on the skin and/or the hair and/or becomes completely or partially liquid due to shear forces and/or dissolves in the filling and/or the skin sebum lipids or as a result of mixing of filling and enveloping material and thus, particularly for the user, is no longer perceptible, particularly as a separate constituent besides the filling.

I.e. the capsule advantageously soaks in during application on the skin or the hair completely without leaving behind residues.

Compared, in particular, with the known cosmetic capsules whose envelope is left behind following application, according to the invention, the sphere described here can remain entirely on the skin. The entire sphere can thus make an active, caring contribution in the cosmetic and dermatological preparation.

Many terms such as "spheres" or "capsules" can in principle be used to describe the preparation according to the invention although different meanings are sometimes assigned to these terms. For example, the terms "praline" or "suppository" are each associated with other, sometimes really non-cosmetic types of application. The term "sphere" or "capsule" for describing the preparation according to the invention is not restricted here to the mathematical meaning, but includes all exactly or approximately, regularly or irregularly ball-shaped, spherical, round, oval, ellipsoidal bodies, likewise those with corners and edges, i.e., for example, cubes, cuboids, parallelepipeds, stars, hearts and the like.

The preparation according to the invention comprises preportioned cosmetic products which are dimensionally stable at room temperature (RT) and which, upon rubbing and/or distribution on the skin and/or the hair, melt, become liquid or dissolve. This ensures that the cosmetic can be applied to the skin or the hair without troublesome residues.

Compared to the capsule-shaped preparations known in the prior art, no material constituents of any kind are left behind unused on the skin, which constituents are unsightly, cause unnecessary costs and environmental burdens and, moreover, following product application have to be removed by the consumer. The non-capsule-shaped preparations known from the prior art, such as chocolate or suppositories, are not suitable for topical use since they firstly have an unsuitable melting temperature (the temperature of the skin is sometimes significantly less than that of normal body temperature) and secondly they cannot be rubbed. Thirdly, (with the exception of margarine) they are not emulsions and, as a result of the lack of water, a very unpleasant uncosmetic feel on the skin is caused, in contrast to the present invention. For example, in the case of margarine, a lack of three-dimensional stability during storage is an obstacle to a use within the meaning of the present invention.

The spheres according to the invention have a size, i.e. an average diameter, of from 3 to 40 mm. The preparations according to the invention can have any desired shapes, although they are preferably spherical with a volume of from 0.1 to 20 ml.

The spheres can thus be handled and used individually. The preparations are dimensionally stable as dragees, spheres, spheroids, ellipsoids or otherwise shaped bodies during storage and removal and become liquid only when distributed and/or rubbed on the skin and/or the hair. This is achieved, for example, through the special composition of the lipid phase of the W/O emulsion.

The spherical preparation according to the invention must be solid and dimensionally stable under storage conditions to which cosmetic products are usually subjected, i.e. the shape of the spheres according to the invention must not change as a result, for example, of the effect of gravity or temperature up to 35° C. during storage. Ideally, the spheres do not stick together during storage even if two spheres are in contact for a prolonged period. Should this requirement be technologically impractical, the problem can be solved through an individual packaging of each individual sphere, similar to an individual packing (candy paper). In some instances, it is advantageous to cover the individual spheres with envelopes which improve the three-dimensional stability, prevent or reduce individual spheres from sticking together and/or reduce or prevent the weight loss caused by evaporation of water and/or other readily volatile components.

The sphere material of the preparation according to the invention remains entirely on the skin following application without leaving behind unsightly residues. The preparation according to the invention thus also exhibits advantageous properties of known cosmetic cream, lotion etc. According to the invention, it is of great importance that all of the raw materials from which the sphere is constructed are very well tolerated by the skin. Ideally, they contribute to skincare, for example by strengthening the natural skin barrier and thus preventing the skin from drying out.

Moreover, the composition of the spheres has a decisive influence on the feel of the skin of the consumer when using the preparations according to the invention. It is therefore advantageous to construct the spheres from substances which, upon application, bring about a pleasant feel on the skin.

The technical and sensory requirements for the preparation according to the invention described here extend significantly beyond the usual requirement spectrum for known cosmetic preparations. It is therefore surprising that a preparation according to the invention can be prepared using raw materials which are already known to the person skilled in the art and have already been used in cosmetics.

The following principles should be observed.

On the one hand, it is possible to use lipids whose melting point is close to the skin temperature of 32° C., i.e. between 30° C. and 40° C., for preparing such a preparation according to the invention. On the other hand, by using suitable waxes, polymeric thickeners and/or gel formers from liquid lipid systems it is possible to produce a thixotropic preparation with a high yield point which satisfies the requirements of the described preparation. It is obvious to the person skilled in the art that the stated mixtures, use of lipids with advantageous melting points and use of thixotropic systems with a suitable yield point can be combined together as desired in order to further optimize the properties of the preparation.

Preferably, the preparation consists of a dimensionally stable lipid/emulsifier mixture which comprises dispersed water with a droplet size below 50 micrometers.

By reference to these requirements according to the invention, the person skilled in the art can produce a preparation according to the invention without exercising an inventive activity. The preparation is thus characterized by the property that it melts upon rubbing and/or distribution on the skin and/or the hair and/or becomes completely or partially liquid due to shear forces and/or mixes with the lipids of the skin sebum and/or dissolves therein.

According to the invention, the cosmetic is applied to the skin and/or the hair without a residue. Without a residue here means that no residues of any type remain visible by the naked eye on the skin or the hair.

A plurality of spheres according to the invention can be stored together in a pack made of paper, metal or plastic etc.

or individually or in multiples through further thin packagings similar to candy paper or separately from one another in a blister pack.

Of particular advantage is the combination of the preparations according to the invention with a blister pack which separates the individual spheres from one another during storage and thus prevents individual spheres from joining together. This can also be achieved by wrapping the individual spheres with thin films made of paper, metal or plastic. Furthermore, the preparations can be packaged in tubes made, for example, of polystyrene, or be sealed into films. Besides films made of cellophane, aluminum and paper, it is also possible to use plastic films. In general, PE (degree of polymerization of 3000-4000) serves as material for such packagings. Further options are press-through packs in which, for example, an aluminum foil is sealed onto a plastic film, or shrink packs. The preparations can, for example, also be introduced into folding boxes, cartons, cans, or plastic bags.

Individual spheres according to the invention can be taken out by simply removing them by hand. According to the invention, the spheres have a handlable size. However, it is also possible to facilitate the removal of the preparation according to the invention through a suitable dispenser system. For this purpose, for example, individual spheres can be released from the dispenser system by operating a simple mechanism. Examples of these are the dispenser systems for candy and other confectionery sold by PEZ International AG under the name "PEZ".

Also advantageous are, however, dispenser systems in which the spheres are stored in indentations in spirals on a round disk and can be removed individually via a dosing mechanism. Of particular advantage here are embodiments which, from their outer shape, are reminiscent of known cosmetic products, for example the known NIVEA can, since this reduces the risk of confusion with foods.

During use, individual spheres are removed and rubbed on the skin. As a result of melting, shearing or dissolution of the solid product constituents, the product becomes less viscous and is readily spreadable and dissolves on or in the skin or the hair. The person skilled in the art will appreciate that it is perfectly possible for the preparation according to the invention to comprise solid constituents whose dissolution during application is neither possible nor desired, namely solids as are already used in conventional cosmetics without the consumer noticing that they are present in solid form. Examples thereof are fillers, sunscreen pigments and colored pigments.

The user removes one or more of the spheres and rubs it on the skin as is otherwise customary with skin cream from a can or tube. However, it is advantageous here that a preportioned amount can be used without excess residues and packaging.

The advantage of the preparation according to the invention is the convenient simple single use for inbetween times. Similarly to applying makeup or balm to the lips, a rubbing in of cream or skin care is thus also possible while on the move. Moreover, the consumer can also offer individual spheres to other consumers. Although this is also possible with conventional cosmetic products, the common use of, for example, a cream from one and the same pot amounts psychologically to body contact. An inhibition threshold therefore exists here which is overcome by the present invention.

It is also possible to supply spheres according to the invention with different properties (e.g. perfume, color, skin feel, sunscreen factor, active ingredients present and combinations of these properties) in one packaging, which is not possible with conventional skin care products.

A further advantage is that the use of the spheres according to the invention is more fun for some users, especially children, than the use of conventional cosmetic products. This can make it easier for parents to protect their children against harmful environmental effects such as, for example, UV radiation.

The person skilled in the art is aware that there is a severe problem in protecting cosmetic products against fungi, yeasts and bacteria which enter the product during use. This happens especially as a result of the product being touched by the consumer during removal. It is obvious that the spheres according to the invention offer a further advantage here since the consumer only touches those spheres which he or she applies immediately. The other spheres remain protected against microbial attack, for which reason it is possible for the contents of preservatives to be lower compared with conventional cosmetic products. Since preservatives are a type of cosmetic raw material which is not very well tolerated, it is thus possible to achieve improved compatibility of the products, which constitutes a further advantage of the present invention.

The spherical preparation can be composed of waxes, fats, oils, silicone oils, water, glycerol and other polyols, and also other water-soluble or oil-soluble active ingredients, auxiliaries or additives. The sphere has adequate impact stability to withstand mechanical stresses during production and storage, and is thin enough to be distributed quickly on the skin during application.

The lipid phase of the spheres is advantageously constructed from waxes such as ceresine, ozokerite, ester waxes, glyceride waxes and/or fatty alcohols, and also solid emulsifiers and mixtures thereof. The waxes may be natural waxes, modified natural waxes, partially synthetic or completely synthetic, depending on their origin.

All of the constituents are chosen so that they ensure the required shape and temperature stability, prevent the filling from drying out as a result of evaporation and rapidly melt upon application, become completely or partially liquid due to shear forces or dissolve in the filling material.

To optimize the elastic properties, polymers can be incorporated into the preparation. Suitable polymers are cellulose ether, polyvinylpyrrolidone and its derivatives, polyacrylates or polymethacrylates, and Eudragit.

The sphere according to the invention is preferably composed of waxes which are chosen from the group of
- natural waxes, particularly preferably carnauba wax, candelilla wax, shellac wax, berry wax (*Rhus Verniciflura*), shea butter (*Butyrospermum Parkii*), hydrogenated vegetable oils, such as hydrogenated palm oil or rapeseed oil, beeswax, wool wax (Eucerit)
- mono-, di- and triglycerides of higher saturated fatty acids having 10-30 carbon atoms or mixtures thereof, particularly preferably glyceryl tripalmitate (Dynasan 116) and/or glyceryl stearate, glyceryl tribehenate (Syncrowax HRC)
- higher saturated fatty alcohols, particularly preferably those having 14-30 carbon atoms, very particularly preferably stearyl alcohol and/or behenyl alcohol and/or cetyl alcohol
- synthetic esters, preferably C16-36 alkylhydroxystearoyl stearate, stearyl stearate, cetearyl behenate, C20-40 alkyl stearate, particularly preferably cetyl palmitate, methyl palmitate, myristyl myristate, cetyl ricinoleate
- polymer waxes, preferably polyethylene, polypropylene, polyvinyl ether, polydecene, particularly preferably polyvinyl stearyl ether and hydrogenated polydecene, copolymers, particularly preferably those of ethylene acetate and vinyl acetate, and of polyvinylpyrrolidone and hexadecene, hydrocarbons/paraffin waxes, particularly preferably Cera Microcristallina, paraffin wax, ceresine, ozokerite silicone waxes chemically modified waxes any mixtures of waxes of the groups mentioned.

Waxes particularly preferred according to the invention for producing the preparation according to the invention are cetyl palmitate, cetyl ricinoleate, beeswax, hydrogenated cocoglycerides, methyl palmitate, candelilla wax, carnauba wax, paraffin wax, ceresine, ozokerite, myristyl myristate, tripalmitin, tribehenin, glyceryl palmitostearate, hydrogenated rapeseed oil and C15-C40 alkylstearyl stearate.

The spheres according to the invention can comprise the customary auxiliaries and additives which are naturally known to the person skilled in the art and as are customarily used in cosmetics, e.g. preservatives, bactericides, deodorizing substances, antiperspirants, insect repellants, vitamins, agents for preventing foaming, dyes, pigments with a coloring effect, flavorings, denaturants, perfumes, thickeners, softening substances, moisturizers and/or humectants, antioxidants, UV filter substances, sensory additives, film formers, surfactants, emulsifiers, fats, oils, waxes, active ingredients or other customary constituents of a cosmetic formulation, such as alcohols, polyols, stabilizing polymers, foam stabilizers, electrolytes, organic solvents or silicone derivatives.

Advantageous W/O emulsifiers which may be used are: fatty alcohols having from 8 to 30 carbon atoms, monoglycerol esters of saturated and/or unsaturated, branched or unbranched alkanecarboxylic acids with a chain length of from 8 to 24, in particular 12 to 20, carbon atoms, diglycerol esters of saturated and/or unsaturated, branched or unbranched alkanecarboxylic acids with a chain length of from 8 to 24, in particular 12 to 20, carbon atoms, monoglycerol ethers of saturated and/or unsaturated, branched or unbranched alcohols with a chain length of from 8 to 24, in particular 12 to 20, carbon atoms, diglycerol ethers of saturated and/or unsaturated, branched or unbranched alcohols with a chain length of from 8 to 24, in particular 12 to 20, carbon atoms, polypropylene glycol esters of saturated and/or unsaturated, branched or unbranched alkanecarboxylic acids with a chain length of from 8 to 24, in particular 12 to 20, carbon atoms, polyglyceryl esters of saturated and/or unsaturated, branched or unbranched alkanecarboxylic acids with a chain length of from 8 to 24, in particular 12 to 20, carbon atoms, sorbitan esters of saturated and/or unsaturated, branched or unbranched alkanecarboxylic acids with a chain length of from 8 to 24, in particular 12 to 20, carbon atoms, lanolin alcohol.

Preferred W/O emulsifiers are polyglyceryl-3 diisostearate, polyglyceryl-4 isostearate, polyglyceryl-2 dipolyhydroxystearate, cetyl PEG/PPG-10-1 dimethicone, PEG-30 dipolyhydroxystearate, PEG40 sorbitan perisostearate, cetyldimethicone copolyol, PEG-7 hydrogenated castor oil, PEG 45/dodecyl glycol copolymer, PEG 22/dodecyl glycol copolymer, pentaerythritol isostearate, isostearyldiglyceryl succinate, sorbitan isostearate, polyglyceryl-2 sesquiisostearate, glyceryl isostearate, sorbitan stearate, glyceryl stearate, PEG-25 hydrogenated castor oil, PEG-40 sorbitan peroleate, sorbitan oleate, PEG-40 sorbitan perisostearate, polyglyceryl-3 oleate, polyglyceryl-2 sesquioleate and polyglyceryl-4 isostearate.

Particularly preferred W/O emulsifiers are polyethylene glycol-45/dodecyl glycol copolymer, polyglyceryl-3 diisostearate, PEG-30 dipolyhydroxystearate, sorbitan isostearate, sorbitan stearate, glyceryl isostearate, glyceryl stearate and sorbitan oleate.

It is also possible to dispense with the lowering of the interfacial energy through emulsifiers or surfactants and instead to stabilize the interface by adding particles which are insoluble in both phases. For this purpose it is possible to use natural or synthetic polymers (polyethylene, nylon, starch and its derivatives) or inorganic particles ($TiO_2$, $Al_2O_3$, $BaSO_4$, BN, silicates, alumosilicates, $SiO_2$, Aerosil).

The oil phase, the lipids, of the formulations according to the invention is advantageously chosen from the group of polar oils, for example from the group of lecithins and of fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, cocoglyceride, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

For the purposes of the present invention, further advantageous polar oil components can also be chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length of from 3 to 30 carbon atoms. Such ester oils can then advantageously be chosen from the group consisting of octyl palmitate, octyl cocoate, octyl isostearate, octyl dodecyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can be chosen advantageously from the group of dialkyl ethers and dialkyl carbonates; advantageous are, for example, dicaprylyl ether (Cetiol OE) and/or dicaprylyl carbonate, for example that available under the trade name Cetiol CC.

It is also preferred to choose the oil components from the group consisting of isoeicosane, neopentyl glycol diheptanoate, propylene glycol dicaprylate/dicaprate, caprylic/capric/triglycerides, caprylic/capric/diglyceryl succinate, butylene glycol dicaprylate/dicaprate, $C_{12-13}$-alkyl lactate, di-$C_{12-13}$-alkyl tartrate, triisostearin, dipentaerythritol hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or consists entirely of this.

Advantageous oil components are also, for example, butyloctyl salicylate (for example that available under the trade name Hallbrite BHB), hexadecyl benzoate and butyloctyl benzoate and mixtures thereof (Hallstar AB) and/or diethylhexyl naphthalate (Hallbrite TQ or Corapan TQ from H&R).

Any mixtures of such oil and wax components can also be used advantageously for the purposes of the present invention.

In addition, the oil phase can likewise advantageously also comprise nonpolar oils, for example those which are chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a catenated and/or reticular manner and the remaining valencies of silicon are saturated by hydrocarbon radicals (mostly methyl groups, more rarely ethyl, propyl, phenyl groups etc.). Systematically, the silicone oils are referred to as polyorganosiloxanes. The methyl-substituted polyorganosiloxanes, which constitute the most important compounds of this group in terms of amount and are characterized by the following structural formula

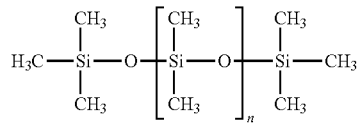

are also referred to as polydimethylsiloxane or Dimethicone (INCI). Dimethicones are available in various chain lengths and with various molecular weights.

Particularly advantageous polyorganosiloxanes for the purposes of the present invention are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to as cyclomethicones in accordance with INCI, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are obtainable as various Abil wax grades from Th. Goldschmidt. However, other silicone oils can also be used advantageously for the purposes of the present invention, for example cetyldimethicone, hexamethylcyclotrisiloxane, polydimethylsiloxane, poly(methylphenylsiloxane).

It is likewise advantageous to add customary antioxidants to the preparations for the purposes of the present invention. According to the invention, favorable antioxidants which may be used are all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, retinoids, such as, for example, retinol, retinal and/or retinoic acid and the respective esters, α-lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxyacids (e.g. citric acid, lacetic acid, malic acid), humic acid, bile acid, bile extracts, bilirubin, biliverdin, EDTA, IDS, EGTA and derivatives thereof, unsaturated fatty acids and derivatives thereof (e.g. γ-linolenic acid, linoleic acid, oleic acid), folic acid and derivatives thereof, 2-aminopropionic acid, diacetic acid, flavonoids, polyphenols, alpha-glycosylrutin, propyl gallate, catechins, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and coniferyl benzoate of benzoin resin, rutinic acid and derivatives thereof, ferulic acid and derivatives thereof, butylated hydroxytoluene, butylated hydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of these specified active ingredients.

The amount of antioxidants (one or more compounds) in the preparations is preferably from 0.001% to 30% by weight, particularly preferably 0.05-20% by weight, in particular 0.1-10% by weight, based on the total weight of the preparation.

If vitamin E and/or derivatives thereof are the antioxidant or the antioxidants, it is advantageous to choose their particular concentrations from the range from 0.001-10% by weight, based on the total weight of the formulation.

In addition, UV filter substances can be added to the preparation according to the invention. It is thus preferred to use the preparations according to the invention as sunscreen formulations.

Particularly advantageous UV filter substances which are liquid at room temperature for the purposes of the present invention are homomenthyl salicylate (INCI: Homosalate), 2-ethylhexyl 2-cyano-3,3-diphenylacrylate (INCI: Octocrylene), 2-ethylhexyl 2-hydroxy-benzoate (2-ethylhexyl salicylate, octyl salicylate, INCI: Octyl Salicylate) and esters of cinnamic acid, preferably 2-ethylhexyl 4-methoxycinnamate (INCI: Octyl Methoxycinnamate) and isopentyl 4-methoxycinnamate (INCI: Isoamyl p-Methoxycinnamate).

Preferred inorganic pigments are metal oxides and/or other metal compounds which are insoluble or sparingly soluble in water, in particular oxides of titanium (TiO$_2$), zinc (ZnO), iron (e.g. Fe$_2$O$_3$), zirconium (ZrO$_2$), silicon (SiO$_2$), manganese (e.g. MnO), aluminum (Al$_2$O$_3$), cerium (e.g. Ce$_2$O$_3$), mixed oxides of the corresponding metals and mixtures of such oxides, and also the sulfate of barium (BaSO$_4$).

For the purposes of the present invention, the pigments may advantageously also be used in the form of commercially available oily or aqueous predispersions. Dispersion auxiliaries and/or solubilizers may advantageously be added to these predispersions.

According to the invention, the pigments can advantageously be surface-treated ("coated"), the aim being to form and/or retain, for example, a hydrophilic, amphiphilic or hydrophobic character. This surface treatment can consist in providing the pigments with a thin hydrophilic and/or hydrophobic inorganic and/or organic layer by methods known per se. For the purposes of the present invention, the various surface coatings can also comprise water.

Inorganic surface coatings for the purposes of the present invention can consist of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings can be present on their own, in combination and/or in combination with organic coating materials.

Organic surface coatings for the purposes of the present invention can consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of from 200 to 350 dimethylsiloxane units and silica gel) or alginic acid. These organic surface coatings may be present on their own, in combination and/or in combination with inorganic coating materials.

Zinc oxide particles and predispersions of zinc oxide particles suitable according to the invention are available under the following trade names from the companies listed:

| Trade name | Coating |
| --- | --- |
| Z-Cote HP1 | 2% dimethicone |
| Z-Cote | / |
| ZnO NDM | 5% dimethicone |

Suitable titanium dioxide particles and predispersions of titanium dioxide particles are available under the following trade names from the companies listed:

| Trade name | Coating |
| --- | --- |
| MT-100TV | aluminum hydroxide/stearic acid |
| MT-100Z | aluminum hydroxide/stearic acid |
| Eusolex T-2000 | alumina/simethicone |
| Titanium dioxide T805 (Uvinul $TiO_2$) | Octyltrimethylsilane |

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsole 1789 and under the trade name Eusolex® 9020.

Likewise suitable UV-A filter substances are hydroxybenzophenones. These are characterized by the following structural formula:

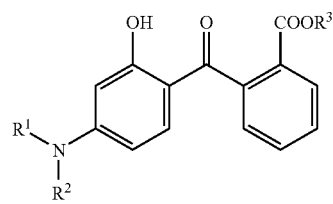

in which
R¹ and R², independently of one another, are hydrogen, $C_1$-$C_{20}$-alkyl, $C_3$-$C_{10}$-cycloalkyl or $C_3$-$C_{10}$-cycloalkenyl, where the substitutents R¹ and R², together with the nitrogen atom to which they are bonded, can form a 5- or 6-membered ring and
R³ is a $C_1$-$C_{20}$-alkyl radical.

A particularly advantageous hydroxybenzophenone for the purposes of the present invention is hexyl 2-(4'-diethylamino-2'-hydroxybenzoyl)benzoate (also: aminobenzophenone), which is characterized by the following structure:

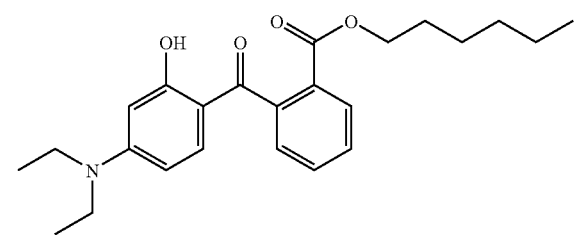 [SMILES: CCCCCCOC(=O)c1ccccc1C(=O)c1ccc(N(CC)CC)cc1O]

and is available under the Uvinul A Plus from BASF.

The total amount of one or more hydroxybenzophenones in the finished cosmetic or dermatological preparations is advantageously chosen from the range of form 0.01% by weight to 20% by weight, preferably from 0.1% to 10% by weight, in each case based on the total weight of the preparations.

Advantageous further UV filter substances for the purposes of the present invention are sulfonated, water-soluble UV filters, such as, for example:

phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name Bisimidazylate (CAS No.: 180898-37-7), which is available, for example, under the trade name Neo Heliopan AP;

salts of 2-phenylbenzimidazole-5-sulfonic acid, such as its sodium, potassium or its triethanolammonium salt and the sulfonic acid itself with the INCI name Phenylbenzimidazole Sulfonic Acid (CAS No. 27503-81-7), which is available, for example, under the trade name Eusolex 232 or under Neo Heliopan Hydro;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephtalidene Dicamphor Sulfonic Acid (CAS No.: 90457-82-2) and is available, for example, under the trade name Mexoryl SX;

sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

Advantageous UV filter substances for the purposes of the present invention are also so-called broadband filters, i.e. filter substances which absorb both UV-A and UV-B radiation.

Advantageous broadband filters or UV-B filter substances are, for example, triazine derivatives, such as, for example, 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S;

diethylhexylbutylamidotriazone (INCI: Diethylhexylbutamidotriazone), which is available under the trade name UVASORB HEB;

tris(2-ethylhexyl) 4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Ethylhexyl Triazone), which is sold under the trade name UVINUL® T 150.

An advantageous broadband filter for the purposes of the present invention is also 2,2'-methylenebis(6-(2H-benzotriazol-2-yl)-4-(1,1,3,3-tetramethylbutyl)phenol), which is available under the trade name Tinosorb® M.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)-oxy] disiloxanyl]propyl]phenol (CAS No.: 155633-54-8) with the INCI name Drometrizole Trisiloxane, which is available under the trade name Mexoryl® XL.

The further UV filter substances may be oil-soluble or water-soluble.

Advantageous oil-soluble UV-B and/or broadband filter substances for the purposes of the present invention are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bound to polymers.

3-(4-(2,2-bisethoxycarbonylvinyl)phenoxy)propenyl) methoxysiloxane/dimethylsiloxane copolymer, which is available, for example, under the trade name Parsol® SLX.

Advantageous water-soluble filter substances are, for example:

Sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

A further photoprotective filter substance to be used advantageously according to the invention is ethylhexyl 2-cyano-3,3-diphenylacrylate (Octocrylene), which is available under the name Uvinul® N 539.

Particularly advantageous preparations for the purposes of the present invention which are characterized by high or very high UV-A and/or UV-B protection comprise, besides the filter substance(s) according to the invention, preferably also further UV-A and/or broadband filters, in particular dibenzoylmethane derivatives [for example 4-(tert-butyl)-4'-methoxydibenzoylmethane], phenylene-1,4-bis(2-benzimidazyl)-3,3'-5,5'-tetrasulfonic acid and/or its salts, 1,4-di(2-oxo-10-sulfo-3-bornylidenemethyl)benzene and/or salts thereof and/or 2,4-bis{[4-(2-ethylhexyloxy)-2-hydroxy]phenyl}-6-(4-methoxyphenyl)-1,3,5-triazine, in each case individually or in any combinations with one another.

The list of specified UV filters which can be used for the purposes of the present invention is not of course intended to be limiting.

Advantageously, the preparations according to the invention comprise the substances which absorb UV radiation in the UV-A and/or UV-B region in a total amount of from, for example, 0.1% by weight to 30% by weight, preferably 0.5% to 20% by weight, in particular 1.0% to 15.0% by weight, in each case based on the total weight of the preparations, in order to make available cosmetic preparations which protect the hair and/or the skin from the entire range of ultraviolet radiation. They can also serve as sunscreens for the hair.

Preparations according to the invention in the form of emulsions particularly advantageously comprise one or more hydrocolloids. These hydrocolloids can be chosen advantageously from the group of gums, polysaccharides, cellulose derivatives, silica and aerosils, sheet silicates, polyacrylates and/or other polymers.

The gums include plant or tree saps which harden in the air and form resins or extracts of aquatic plants. From this group, for the purposes of the present invention, it is advantageous to choose, for example, gum arabic, carob-seed flour, tragacanth, karaya, guar gum, pectin, gellan gum, carrageen, agar, algins, chondrus, xanthan gum.

Also advantageous is the use of derivatized gums, such as, for example, hydroxypropyl guar (Jaguar® HP 8).

The polysaccharides and polysaccharide derivatives include, for example, hyaluronic acid, chitin and chitosan, chondroitin sulfates, starch and starch derivatives.

The cellulose derivatives include, for example, methylcellulose, carboxymethylcellulose, Hydroxyethylcellulose, hydroxypropylmethylcellulose.

The sheet silicates include naturally occurring and synthetic clay earths, such as, for example, montmorillonite, bentonite, hectorite, laponite, magnesium aluminum silicates, such as Veegum®. These can be used as they are or in modified form, such as, for example, stearylalkonium hectorite.

In addition, silica gels can also be used advantageously, which can be prepared, for example, using fumed silica (for example the Aerosil grades 200, 300, 800, R 812 or R 972).

Also advantageous are taurates, e.g. ammonium acryloyidimethyltaurateNP copolymer.

The polyacrylates include, for example, Carbopol grades (Carbopol 980, 981, 1382, 5984, 2984, ETD 2001, ETD 2020, ETD 2050, Ultrez-10 or Pemulen TR1 & TR2).

The polymers include, for example, polyacrylamides (Seppigel 305), polyvinyl alcohols, PVP, PVPNA copolymers, polyglycols.

The water phase of the preparations according to the present invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, butylene glycol, ethylene glycol, ethylene glycol monoethyl or monobutyl ether, propylene glycol monomethyl, monoethyl or monobutyl ether, diethylene glycol monomethyl or monoethyl ether, ethylhexyloglycerol, methylpropanediol and analogous products, polymers, foam stabilizers, electrolytes, such as, for example, sodium chloride or magnesium sulfate, and in particular one or more thickeners, which can be chosen advantageously from the group consisting of silicon dioxide, alumosilicates, polysaccharides and derivatives thereof, e.g. hyaluronic acid, xanthan gum, hydroxypropylmethylcellulose, particularly advantageously from the group of polyacrylates, preferably a polyacrylate from the group of so-called Carbopols, for example Carbopol grades 980, 981, 1382, 2984, 5984, ETD 2020, ETD 2050, Ultrez 10, in each case individually or in combination.

In addition, the preparations according to the present invention may advantageously also comprise self-tanning substances, such as, for example, dihydroxyacetone and/or melanine derivatives, in concentrations of from 0.1% by weight up to 10% by weight, based on the total weight of the preparation.

In addition, the preparations according to the present invention can advantageously also comprise repellents for protecting against flies, ticks and spiders and the like. Of advantage are, for example, N,N-diethyl-3-methylbenzamide (trade name: Metadelphene, "DEET"), dimethyl phthalate (trade name: Palatinol M, DMP), and in particular ethyl 3-(N-n-butyl-N-acetylamino)propionate (available under the trade name Insect Repellent® 3535). The repellents can either be used individually or in combination. Aromatic oils or the like can likewise be used.

Humectants and/or skin-moisturizers are the terms used to refer to substances or mixtures of substances which impart to cosmetic or dermatological preparations the property, following application and/or distribution on the surface of the skin, of reducing the release of moisture by the horny layer (also termed transepidermal water loss (TEWL)) and/or of positively influencing hydration of the horny layer. Advantageous moisturizers for the purposes of the present invention are, for example, glycerol, lacetic acid and/or lactates, in particular sodium lactate, butylene glycol, propylene glycol, panthenol, fucogel, glycine soya, ethylhexyloxyglycerol, pyrrolidonecarboxylic acid and its derivatives, and urea. In addition, it is particularly advantageous to use polymeric moisturizers from the group of water-soluble and/or water-swellable and/or water-gellable polysaccharides. In particular, hyaluronic acid, chitosan and/or a fucose-rich polysaccharide which is deposited in the Chemical Abstracts under the registry number 178463-23-5 is available, for example, under the name Fucogel® 1000, for example, are advantageous. Moisturizers can advantageously also be used as antiwrinkle active ingredients for the prophylaxis and treatment of cosmetic or dermatological changes in the skin, as arise, for example, during skin aging.

The cosmetic or dermatological preparations according to the invention can also advantageously, although not necessarily, comprise fillers which, for example, further improve the sensory and cosmetic properties of the formulations and, for example, bring about or enhance a velvety or silky feel on the skin. Advantageous fillers for the purposes of the present invention are starch and starch derivatives (such as, for example, tapioca starch, distarch phosphate, aluminum or sodium starch octenylsuccinate and the like), pigments which have neither primarily UV filter effect nor coloring effect (such as, for example, boron nitride etc.) and/or Aerosils® (CAS No. 7631-86-9).

For use, according to the invention, the spherical preparations are applied to the skin and/or the hair in the manner customary for cosmetics and rubbed or distributed.

Besides the constituents according to the invention, the cosmetic and/or dermatological preparations according to the invention can be composed like customary cosmetic and/or dermatological preparations and serve for cosmetic and/or dermatological photoprotection, for changing or influencing certain skin conditions, also for the treatment, care of the skin and/or of the hair and as a make-up product in decorative cosmetics.

Accordingly, cosmetic and/or topical dermatological compositions for the purposes of the present invention can, depending on their formulation, be used, for example, as skin care product, skin protection product, sunscreen product, hair treatment, for day or night care, the care of certain areas of skin, such as hands, face, feet etc.

The use of the spherical cosmetic preparations according to the invention for the prophylaxis and treatment of the symptoms of aging skin, for preventing and reducing the formation and spread of wrinkles and lines, and for the treatment and care of aged skin is also in accordance with the invention. Thus, an individual capsule comprising ubiquinone, ubiquinol, retinol and derivatives, dehydroepiandrosterone (DHEA), isoflavonoids (in particular genistein, daidzein), creatin, phytoestrogens, estrogen, estradiol and derivatives, niacinamide, polyphenols (alpha-glucosylrutin) or another substance effective against lines can advantageously be applied and distributed on the facial skin.

In addition, the use of the spherical cosmetic preparations according to the invention for the prophylaxis and treatment of the symptoms of dry skin is preferred. Suitable active ingredients for this use purpose are: natural oils (sunflower oil, evening primrose-seed oil, jojoba oil, macadamia oil, castor oil), ceramides, in particular ceramide I, III and VI, cholesterol, phytosterols, fatty acids with a chain length of C16-26, in particular linoleic acid, carnitine and its derivatives, urea, polyols such as glycerol, butylene glycol, propylene glycol and dipropylene glycol, pseudoceramides; electrolytes, such as sodium chloride and taurine, fatty alcohols, and waxes.

Furthermore, the use of the spherical cosmetic preparations according to the invention for the prophylaxis and treatment of the symptoms of sensitive and/or inflamed skin is advantageous. Preferred active ingredients for this intended use are: ingredients of milk thistle, in particular silymarin, hamamelis extract, camomile extract, ingredients of the liquorice plant (glycerrhicinic acid), acetylsalicylic acid, diclofenac, pentacyclic triterpenes (sericosides, urolic acid), licochalcones and panthenol.

Furthermore, the use of the spherical cosmetic preparations according to the invention for the prophylaxis and treatment of the symptoms of incorrectly pigmented skin is advantageous. Preferred active ingredients for this intended use are: tyrosinase inhibitors, hydroquinone derivatives, dioic acid, lipoic acid and its derivatives, and kojic acid.

It is in some cases possible and advantageous to use the compositions according to the invention as a base for pharmaceutical formulations. In addition, the use of the spherical cosmetic preparations according to the invention for the prophylaxis and treatment of the symptoms of diseased skin is preferred. Relevant but nonexclusive diseased skin conditions are psoriasis, acne, neurodermitis and other atopic disorders, such as atopic dermatitis, skin cancer, herpes, mycoses, ichthyosis, pityriasis, seborrhoea, pellagra, contact eczema and allergies. Suitable active ingredients for such intended uses are antibiotics, such as fusidic acid, erythromycin, sulfadiazine, clindamycin, tetracyclines, tyrothricin aminoglycosides, bacitracin, chloramphenicol, virostatics (e.g. acyclovir, idoxuridin, penciclovir), antimycotics (e.g. nystatin, amphotericin, clotrimazole, econazole, ketoconazole, naftifin, terbinafin), allethrin, cytostatics (5-fluorouracil), antiphlogistics (hydrocortisone, betamethasone; prednisolone, triamcinolone acetonide, dexamethasone, diclofenac, bufexamac), immunosuppressants (cyclosporine A, interferon-beta), antipsoriatics (dithranol, psoralene, tazarotene), acne agents (retinoic acid, isotretinoin, benzoyl peroxide, adapalene); capsaicin, azelaic acid, keratolytics (salicylic acid, lacetic acid), antihistamines (azelastin, levocabastin, disodium cromoglycine); antipsoriatics (dithranol, calcitriol, psoralene) and vitamins (particularly the A, B and C vitamins).

One possible use which is advantageous according to the invention is to supply spheres with different intended uses in one pack, for example those for day care and night care, those with different colors, fragrances, different-strength sunscreen factors or different active ingredients. With such a use, it is particularly advantageous to make the spheres with a different composition distinguishable for the user through different shaping and/or coloring.

Last but not least, the use of the cosmetic and/or dermatological preparations according to the invention for the prophylaxis and treatment of greasy skin, and also for the prophylaxis and treatment of blemished skin and of cellulite is in accordance with the invention.

The production of the spherical preparations according to the invention is described below by way of example and consists firstly in producing a W/O emulsion from the constituents essential to the invention with the subsequent use of shaping methods.

The production of emulsions from lipid and water phases which are not miscible with one another has been known for a long time and generally takes place by introducing mechanical energy through the use of suitable stirrers and homogenizers. Since the emulsions according to the invention are solid at room temperature, all of the processing steps (addition and mixing of the ingredients, homogenization, any defoaming by applying a vacuum) have to be carried out at temperatures above the melting point of the lipid phase. As a rule, it is of no importance whether the lipid phase is added first or the water phase is added first. However, when using non-optimized plants and formulae, it may prove to be advantageous for the production of a W/O emulsion to initially introduce the lipid phase.

For example, the formulation described as Example 1 can be prepared in the following way: ceresine, methyl palmitate, polyethylene, PEG-45/dodecyl glycol copolymer, polyglyceryl-3 diisostearate, dimethicone, phenoxyethanol and hexamidine diisethionate are melted with stirring and heated to 70° C. (lipid phase). Na EDTA, alpha-glycosylrutin, glycerol, ascorbylpalmitate, dye, and citric acid are dissolved in water and the solution is heated to 70° C. (water phase).

The water phase is then added to the lipid phase with stirring, resulting in the formation of a W/O emulsion. This is further cooled with stirring and, at about 50° C., the perfume is added. At about 45° C., stirring is stopped and the emulsion cools further at rest until it finally becomes solid. In some circumstances, this is only the case after prolonged standing at room temperature since the emulsions according to the invention sometimes show tendencies to form a supercooled melt.

The preparation of the other examples takes place accordingly.

For storage and/or transportation, the emulsion produced in this way can be solidified and melted again as often as desired. To shape the spheres according to the invention, the emulsion is either poured into appropriate molds above its melting point and solidified therein, or it is pressed into molds under pressure below its melting point.

The preparation according to the invention has improved sensory properties which are not to be expected with wax-containing preparations from the prior art. Improved distributability, absorptivity, consistency, skin smoothing and reduced stickiness were found. With regard to suitable methods for determining these parameters, reference may be made to the knowledge of the person skilled in the art.

The stated sizes, such as, for example, the diameter of the spheres, are to be understood as meaning the diameter in the direction of the longitudinal expansion of the spheres.

The examples below illustrate the preparations according to the invention. Unless stated otherwise, the percentage data refer to the total mass of the preparations.

Example 1

| | |
|---|---|
| Ceresine | 6% |
| Methyl palmitate | 21% |
| Polyethylene | 3% |
| PEG-45/dodecyl glycol copolymer | 2.5% |
| Polyglyceryl-3 diisostearate | 1.5% |
| Simethicone | 0.5 |
| Phenoxyethanol | 0.5% |
| Hexamidine diisethionate | 0.08% |
| EDTA, Na salt | 0.2% |
| alpha-glycosylrutin | 0.2% |
| Glycerol | 5% |
| Ascorbyl palmitate | 0.1 |
| Dye | q.s. |
| Citric acid | q.s. |
| Perfume | q.s. |
| Water | ad 100 |

Example 2

| | |
|---|---|
| Ozokerite | 3% |
| Shea butter | 21% |
| Polyethylene | 3% |
| PEG-45/dodecyl glycol copolymer | 1% |
| Polyglyceryl-3 diisostearate | 1% |
| Bisethylhexyloxyphenol methoxyphenyltriazine | 2% |
| Octyl methoxycinnamate | 5% |
| Simethicone | 0.5 |
| Phenoxyethanol | 0.5% |
| Parabens | 0.08% |
| Urea | 3% |
| Glycerol | 6% |
| Lactic acid | q.s. |
| Dye | q.s. |
| Perfume | q.s. |
| Water | ad 100 |

Example 3

| | |
|---|---|
| Hydrogenated cocoglycerides | 10% |
| Caprylyl/caprinyl triglycerides | 25% |
| Polyethylene | 3% |
| Eucerit | 3.0% |
| $TiO_2$ | 2% |
| Aerosil R 812 | 1% |
| Dekaben LMB | 0.5% |
| Phenoxyethanol | 0.3% |
| Ubiquinone | 0.1% |
| Butylene glycol | 3.0% |
| Panthenol | 3.0% |
| Glycerol | 4% |

-continued

| | |
|---|---|
| Citric acid | q.s. |
| NaOH | q.s. |
| Perfume | q.s. |
| Water | ad 100 |

Example 4

| | |
|---|---|
| Myristyl myristate | 15% |
| Cetyl ricinoleate | 20% |
| Ceresine | 5% |
| Polyglyceryl-3 diisostearate | 1.5% |
| Polyglyceryl-2 dipolyhydroxystearate | 1.5% |
| Mica | 2% |
| DMDM hydantoin | 0.2% |
| Phenoxyethanol | 0.4% |
| Creatine | 0.3% |
| Creatinine | 0.1% |
| Niacinamide | 0.2% |
| Glycerol | 5% |
| Perfume | q.s. |
| Water | ad 100 |

Example 5

| | |
|---|---|
| Paraffinum liquidum | 15% |
| Hydrogenated vegetable fat | 15% |
| Cera Microcristallina | 10% |
| Eucerit | 1% |
| Polyglyceryl-2 dipolyhydroxystearate | 1.5% |
| Nylon | 2% |
| Magnesium stearate | 0.5% |
| Ethylhexyloxyglycerol | 0.5% |
| Parabens | 0.6% |
| Phenoxyethanol | 0.5% |
| Retinyl palmitate | 0.2% |
| Panthenol | 1% |
| Glycerol | 5% |
| Perfume | q.s. |
| Water | ad 100 |

Example 6

| | |
|---|---|
| Paraffinum liquidum | 15% |
| Hydrogenated vegetable fat | 15% |
| Cera Microcristallina | 10% |
| Polyglyceryl-3 diisostearate | 1% |
| PEG-45/dodecyl glycol copolymer | 2% |
| Distarch octenyl succinate | 1% |
| Magnesium stearate | 0.5% |
| Methylpropanediol | 0.5% |
| Parabens | 0.3% |
| Creatine | 0.2% |
| Phenoxyethanol | 0.3% |
| Tocopheryl acetate | 0.5% |
| Glycerol | 5% |
| Iron oxide pigments | 1% |
| Perfume | q.s. |
| Water | ad 100 |

What is claimed is:

1. A cosmetic or dermatological preparation, wherein the preparation comprises a plurality of shaped bodies which consist of a W/O emulsion, are at least one of solid, semisolid and dimensionally stable up to a temperature of at least 35° C. and comprise at least one of a wax, a lipid, an emulsifier, a natural polymer and a synthetic polymer.

2. The preparation of claim 1, wherein the shaped bodies comprise at least one of a sphere and a spheroid.

3. The preparation of claim 1, wherein the shaped bodies comprise one or more waxes selected from microcrystalline waxes, paraffin waxes, ester waxes, glyceride waxes, fatty alcohols, solid emulsifiers and combinations thereof.

4. The preparation of claim 3, wherein the one or more waxes comprise one or more of cetyl palmitate, cetyl ricinoleate, beeswax, hydrogenated cocoglycerides, methyl palmitate, candelilla wax, carnauba wax, paraffin wax, ceresine, ozokerite, myristyl myristate, tripalmitin, tribehenin, glyceryl palmitostearate, hydrogenated rapeseed oil, and C15-C40 alkylstearyl stearate.

5. The preparation of claim 1, wherein the W/O emulsion comprises a dimensionally stable lipid/emulsifier mixture which comprises dispersed water having a droplet size below 50 micrometers.

6. The preparation of claim 2, wherein the shaped bodies have an average diameter of from 3 mm to 40 mm.

7. The preparation of claim 1, wherein the shaped bodies comprise predominantly spherical, round or ellipsoidal shapes.

8. The preparation of claim 7, wherein the shaped bodies have a volume of from 0.1 ml to 20 ml.

9. The preparation of claim 1, wherein the shaped bodies further comprise one or more substances selected from auxiliaries, UV filters, pigments, active ingredients, dyes, sensory additives, thickeners, gel formers, preservatives, antioxidants, complexing agents, flavorings, denaturants, and perfumes.

10. The preparation of claim 2, wherein the shaped bodies are individually enclosed by a packaging envelope.

11. The preparation of claim 2, wherein the shaped bodies are packaged individually or in multiples in a pack made of at least one of paper, metal and plastic.

12. The preparation of claim 11, wherein the pack comprises a blister pack.

13. The preparation of claim 1, wherein the preparation is packaged in ready-made portions in a blister pack for individual removal.

14. The preparation of claim 2, wherein the shaped bodies are packaged in a dispenser system.

15. The preparation of claim 1, wherein the shaped bodies, upon at least one of rubbing and distributing them on the skin or the hair, at least one of
   melt;
   become completely or partially liquid due to shear forces;
   dissolve completely or partially in skin sebum lipids.

16. The preparation of claim 3, wherein the shaped bodies, upon at least one of rubbing and distributing them on the skin or the hair, at least one of
   melt;
   become completely or partially liquid due to shear forces;
   dissolve completely or partially in skin sebum lipids.

17. The preparation of claim 1, wherein the preparation comprises at least two shaped bodies which differ in at least one of their appearance, their ingredients and their purpose.

18. A method of applying at least one of a cosmetic ingredient and a dermatological ingredient to skin or hair, wherein the method comprises at least one of rubbing and distributing on the skin or hair a preparation of claim 1 which comprises the at least one of a cosmetic ingredient and a dermatological ingredient.

19. A method of applying cosmetics without leaving a residue on skin, wherein the method comprises applying the preparation of claim 1 to the skin.

20. The preparation of claim 1, wherein the shaped bodies comprise one or more lipids having a melting point of from about 30° C. to about 40° C.

* * * * *